Figure 1:
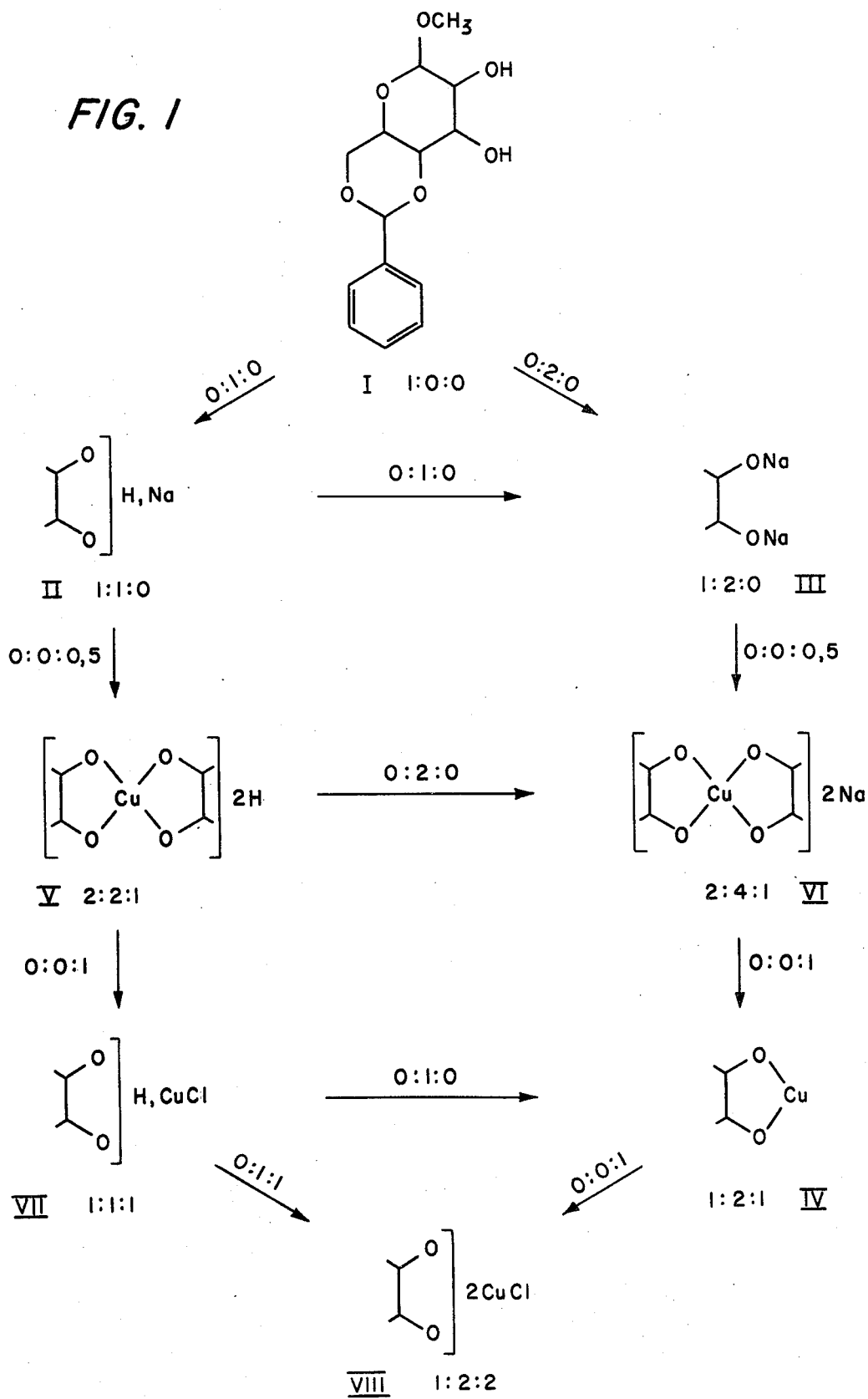

United States Patent [19]

Avela

[11] 3,972,868
[45] Aug. 3, 1976

[54] METHOD FOR SELECTIVELY GUIDING AND LIMITING THE REACTIONS OF HYDROXYL COMPOUNDS

[75] Inventor: Eero Sakari Avela, Helsinki, Finland

[73] Assignee: Suomen Sokeri Osakeyhtio, Helsinki, Finland

[22] Filed: July 19, 1972

[21] Appl. No.: 273,122

[52] U.S. Cl. .............................. 536/18; 260/429 J; 260/429.1; 260/429.2; 260/429.3; 260/429.9; 260/430; 260/431; 260/435 R; 260/438.1; 260/438.5 R; 260/439 R; 260/613 R; 260/615 R

[51] Int. Cl.² ................. C07H 15/00; C07H 15/02; C07C 43/20

[58] Field of Search ........ 260/209 R, 210 R, 234 R, 260/429 J, 438.1, 439 R, 435, 613 R, 438.5, 429.3, 615 R

[56] References Cited
UNITED STATES PATENTS

| | | | |
|---|---|---|---|
| 2,736,725 | 2/1956 | Ritter | 260/210 R |
| 3,074,927 | 1/1963 | Saltman et al. | 260/209 R |
| 3,251,781 | 5/1966 | Jordan | 260/209 R |
| 3,432,489 | 3/1969 | Nitta et al. | 260/234 R |
| 3,563,978 | 2/1971 | Ochs | 260/209 R |
| 3,590,021 | 6/1971 | Bush | 260/209 R |
| 3,591,616 | 7/1971 | Baldt | 260/209 R |
| 3,629,229 | 12/1971 | Schmank | 260/209 R |
| 3,637,657 | 1/1972 | Morii et al. | 260/234 R |
| 3,657,361 | 4/1972 | Lenz et al. | 260/615 R |
| 3,668,273 | 6/1972 | Krantz | 260/613 R |
| 3,686,238 | 8/1972 | Zaffaroni | 260/210 AB |
| 3,694,480 | 9/1972 | Omietanski | 260/210 R |
| 3,697,498 | 10/1972 | Browning et al. | 260/210 R |
| 3,803,250 | 4/1974 | Hartmann | 260/615 R |

*Primary Examiner*—Johnnie R. Brown
*Attorney, Agent, or Firm*—Brumbaugh, Graves, Donohue & Raymond

[57] ABSTRACT

The present invention relates to a method for producing, from a hydroxyl compound, a sequence of metal derivatives, which are subsequently made to react selectively for a certain purpose. The present invention relates to a method for selectively guiding reactions with polyhydroxyl compounds so as to occur at a predetermined hydroxyl group or groups, by carrying out said reactions over complexes of polyvalent metals and wherein the recovery of the parent compounds of the reaction products is achieved by adding water to the mixture after the reaction solvent is distilled off.

17 Claims, 2 Drawing Figures

METHOD FOR SELECTIVELY GUIDING AND LIMITING THE REACTIONS OF HYDROXYL COMPOUNDS

When derivatives are prepared from compounds containing several functional groups which all react with the same reagent, it is decisive to the characteristic features and the uses of the product that either all the functional groups react completely or that a certain degree of substitution is achieved (a) either independently of the location of the substituents or (b) selectively reacting only functional groups of a certain location or type. Unless the functional groups which should not react are protected, the product usually results in a mixture of compounds with different degrees of substitution or a mixture of isomers. A mixture of compounds is usually not as suitable for chemical, technical or biological purposes as is a compound of uniform chemical composition which has reacted completely or specifically. Thus the characteristic features of cellulose ethers and esters, for example, depend not only on the degree of substitution but also on the number and location of substituents on the glucose units. As a further example, the characteristic features of grafted or cross-linked carbohydrate polymers depend on equal or non-equal lengths or on the distribution of the side chains on the backbone polymer.

Similarly, the number and distribution of substituents decide the enzymologic or immunologic reactivity of dextran, the pore size characteristics of cross-linked dextrans used as molecular sieves, and the nature of dextran sulfonates or amine derivatives used as ion exchangers (Norrman, B.: Makromolekyler, Kemisk tidskrift (1969) nr 10,1). Furthermore, the efficiency and type of detergents and emulsifiers utilizing carbohydrate fatty acid esters depend on the number and location of the substituents (Saarnio, J. and Puupponen, L., Kemian Teollisuus (1971) nr 2, 107), the monoesters of mono- and disaccharides being the most effective surfactants in an aqueous environment.

Each hydroxyl group of a polyhydroxy compound, a carbohydrate for example, is of a slightly different character in respect to acidity, inductive effects, hydrogen bonds and steric features. The limiting of the amount of a given reagent attacking the functional group to reach a degree of substitution of D.S.1, gives not only mono- substituted compounds, for example H. M., oligo, and polysaccharides containing several free hydroxyls but also di-, tri- and tetra- substituted compounds. Higher substituted compounds as well as isomers are formed right from the beginning of the reaction. (Croon, I., Svensk Papperstidning 63 (1960) 247). Moreover, by limiting the amount of reagent a corresponding part of the parent compound remains unreacted thus leading to the formation of compounds having an undesirably high degree of substitution. Only with large functional groups, such as diethylaminoethylchloride, is some selectivity reached as to the site of substitution. For example, the hydroxyl group at C-3 of glucosides can primarily be substituted with diethylaminoethylchloride, while the C-2 hydroxyl remains unsubstituted. (Roberts, E. J. and Rowland, S. P., Carbohydrate Research 5 (1967) 1). If on the other hand, there is a free C-6 hydroxyl in a glucoside, this hydroxyl can be selectively tritylated or tosylated. (Flowers, H.M., Protection of Hydroxyl Group, ed. Patai. S., The Chemistry of Hydroxyl Group, Part 2, Interscience Publ., London 1971, pp. 1002–1044).

Selectivity in reactions of polyhydroxyl compounds is usually achieved only by previous protection of certain groups as organic derivatives so that only the desired not masked group or groups should finally react. Due to the multistage protection reactions, reconversion of the reacted parent compounds, solubility of the produced hydroxyl compounds in water, deionization of water solutions, and related procedures, these prior art processes decrease the yield of product to an unacceptable level for preparative and technical use. (Flower, H. M., Protection of Hydroxyl Group, ed. Patai, S., The Chemistry of Hydroxyl Group, Part 2, Interscience Publ., London 1971, pp. 1002–1044). In order to achieve a complete reaction with carbohydrates, it is not unusual to use excessive amounts of reagents and to repeat the operation several times. Further complications arise when aqueous conditions are used during the substitutions, since it is not known with certainty which form of the compound, e.g., alkali hydroxide adduct, alcoholate or chelate, is subjected to reaction. Therefore, this kind of process causes uncontrollable reactions and waste of reagent and time. This is the case in the common methylation of carbohydrates with dimethylsulphate which occurs in 17–30% NaOH, and with epoxide vapor phase reactions on solid alkali treated carbohydrate fabrics.

The present invention consists of a method of obtaining a selective and/or limited reaction of hydroxyl compounds via their stoichiometrically and even structurally exactly definable metal derivatives in completely anhydrous conditions.

The parent compounds in the method of this invention are special metal complexes particularly chelates. The inventor has reported on the formation of these complexes at the meeting of the American Chemical Society in 1960. The reported investigation was based on a study of about 130 compounds containing hydroxyl groups, where the stereochemistry of the functional groups was examined using chelates in non-aqueous solvents, e.g., in tetrahydrofuran (THF). In this method, the ionization of the hydroxyl groups was exactly controlled by sodium hydride, and new types of copper chelates were formed from the sodium alcoholates produced by action of copper (II) chloride. These chelates typically gave colored clear solutions in some organic solvents. (Avela, E., Abstracts of Papers, Am Chem. Soc. 138th Nat. Meeting, New York, Sept. 1960, pp. 18D–19D No. 51). It was characteristic of these metal derivatives that from each hydroxyl compound, a sequence of stoichiometrically exactly definable chelates was formed depending on the structure, configuration and conformation of the compound. The number, colors, and solubility of these chelates were typical for each species of hydroxyl compound in question.

The linkages between the hydroxyl group oxygen and the metal were either covalent, covalent-ionic, or entirely ionic. Now the covalent-ionic and ionic complexes are further subjected to reactions according to the method of this invention.

In accordance with the present invention, the chelate sequences of hydroxyl compounds were more thoroughly investigated. FIG. 1 schematically shows the preparation and interchangeability of these alcoholates and copper derivatives used further as starting material at the now disclosed selective reactions. The compounds are characterized by the mole ratio of glucoside to sodium hydride to copper (II) chloride (glucoside:- $NaH:CuCl_2$) used in the synthesis. The compounds are marked in FIG. 1 with running numbers I, II, III etc. The mole ratio of the components is expressed below each number. The reactions are shown by arrows and there is the mole ratio of the added component above the arrows. Thus the parent hydroxyl compound, here a glucoside, is marked with number I and the mole ratio of its components is expressed with 1:0:0. When the compound I is treated with 1 mole of sodium hydride the mole ratio of the added component is 0:1:0. The mono-sodium alcoholate formed is compound number II and the mole ratio of the compound after its formation is expressed as 1:1:0. As an example, in FIG. 1 there is shown the formation of mono- and disodium alcoholate. Formulae II and III, respectively, have corresponding ratios of reagents of 1:1:0 and 1:2:0. The copper (II) derivatives with formulae IV through VIII have ratios in formation of 1:2:1, 2:2:1, 2:4:1, 1:1:1 and 1:2:, respectively. The formation and interchangeability of the derivatives of a compound containing two free hydroxyl groups are illustrated with the anomeric 4,6-O-benzylidene-D-glucopyranosides in FIG. 1 marked with formula No. I.

Other examples of such chelate sequences include cis-1,2-Cyclopentane-diol in tetrahydrofuran (THF) with copper (II) chloride, which form a green covalent and a green and a blue ionic complex. Only the covalent complex with trans-1,2-Cyclopentane-diol is stable; the ionic complexes immediately polymerize and precipitate. 2-methyl-2,4-pentane-diol in THF forms a copper derivative sequence of a green covalent complex, and a sequence with ionic linkages of orange, green, red, green and blue chelates all of which are formed with exact stoichiometry from the components. Further cobalt (II) chloride in dimethylformamide (DMF) with 2,3-butane-diol forms a series of blue, green and yellow ionic chelates. Pentaerythritol and methyl glucoside do not form chelates in THF but do so in DMF.

The method of this invention consists of selective reaction via the metal derivatives of hydroxyl compounds produced as described above. It is characteristic of the invention that all reactions take place with anhydrous reagents in non-aqueous solvents. Thus the object of this invention is a method where selective or limited reaction of certain hydroxyl groups of those available in the parent compound is acheived through the protection of certain hydroxyl groups by blocking them in the form of a complex, particularly of a polyvalent metal. The degree of ionization of the hydroxyl groups is controlled advantageously by an alkali hydride and derivatives are produced from the thus formed alcoholate with anhydrous salts of polyvalent metals. The expression "polyvalent metal" means here a metal with di-, tri-, or higher valency. These derivatives of hydroxyl compounds react selectively according to this invention.

The method of this invention offers the following advantages which are not achieved by formerly known methods.

A. In the method of this invention the obvious state and location of the hydroxyl grouping which is subjected to the reaction is exactly known, as is the amount and the location of the metal which masks those groups to be protected.

B. The desired reaction can be controlled and achieved without using excess of the reagent.

C. As the reactions take place in organic solvents in completely anhydrous conditions, the solvent is easily recovered by distillation and the parent compound as well as the reaction products are recovered by nearly quantitative yield.

D. The multistage protection of certain hydroxyl groups as organic derivatives, such as ethers, esters and acetals as well as the recoversion reactions, all of which decrease the final yield, are avoided. According to the method which is the object of this invention the reaction products are recovered from the protecting metal derivatives by addition of water, alkali, acid or the like. Deionization by ion exchangers of the reacted large volumes of aqueous solutions typical of prior art methods is here avoided as is the distillation of water. After evaporation of the organic reaction solvent, the addition of only a minute amount of water is required to hydrolyze and dissolve the metal derivatives. The extraction by organic solvents of this very limited water solution volume gives a high yield of products.

The compounds which are affected by the selective reactions according to this method have more than one hydroxyl group or in addition to one hydroxyl, other functional groups which may instead of oxygen contain sulpur or nitrogen, for example:

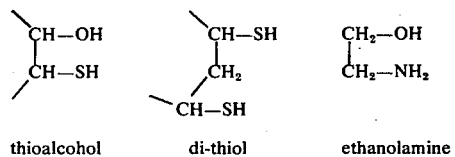

thioalcohol    di-thiol    ethanolamine

The reaction may be adapted to all kinds of polyhydroxyl compounds containing hydroxyl compounds may have an open chain structure or they may be homo- or heterocyclic di-, tri- or polyjydric alcohols. Examples of different types are the aliphatic synthetic diols, glycerol and the carbohydrates. Furthermore, the reaction is suitable for polyhydric ether alcohols such as triethyleneglycol, hydroxy aldehydes and hydroxy ketones for example, sugars, diketones in the enol-form, polyketones such as acetylacetone, polyaldehydes, polyhydric phenols e.g., pyrocathecol, phenol carboxylic acids and their derivatives e.g., methylsalicylate, halogentated alcohols e.g., 1-chloro-2, 3-propanediol, hydroxy and ketoacids and their esters such as ethylacetoacetate, as well as other derivatives of carboxylic acids.

Some or all of the functional groups of the compounds mentioned above are transformed into metal complexes or chelates of a di-, tri- or polyvalent metal according to the method described above (FIG. 1). The general form of the derivatives of divalent metals is e.g., —O—Me—X, —O—Me—o or

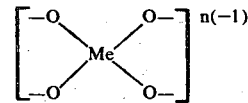

where X is a halogen, sulphate or other anion, Me is the metal and n is the total number of valences. The electric charge signs as well as the differing nature of metaloxygen bond markings are omitted. The reaction The unreacted excess of methyl iodide and the THF are recovered by distillation. The green residue, which is insoluble in organic solvents, is dissolved in a small protion concentrated ammonia and crushed ice and the solution is extracted repeatedly with ethyl acetate. The combined extracts are treated with small portions of 2N $H_2SO_4$ and washed with concentrated $Na_2S_2O_3$, dried with $Na_2SO_4$ and the EtOAc is removed by distillation. The paraffin oil, which remains from the NaH is removed from the residue by petrol ether. The yield is 280–290 g. or 90–99% yellow or white crystals m.p. 155°C, which according to a gas chromatographic analysis contains exclusively monoether, 80% of which is 3-O methyl ether and the rest 2-O methyl ether.

The copper derivatives 1:1:1 and 1:2:2 form from both anomers a green solution, which reacts in DMF forming monoether only, the reaction being slower than with the 1:2:1 chelate. (If the disodium alcoholate mentioned above is methylated without chelating, in THF or DMF at 65°C merely di-O-methyl ether is formed in about 20 minutes).

EXAMPLE II

If in the reaction described in Example I $CoCl_2$ is used instead of $CuCl_2$ and dimethyl formamide is used as the solvent, an almost quantitative yield is achieved, of which 93% is 3-O methyl ether and 7% 2-O methyl ether.

EXAMPLE III

To 150 g (1 mole) of triethylene glycol in 1 litre of anhydrous THF, 96 g (2 moles) of 50% oil dispersion of sodium hydride is slowly added. The formed disodium alcoholate is transformed into a soluble chelate by adding 130 g (1 mole) of anhydrous cobalt (II) chloride, After the addition of 120 ml (2 moles) of methyl iodide the mixture is refluxed with a condenser equipped with a $CaCl_2$ tube for one day. The yield is 155 g. or 95% of the theoretical. According to the gas chromatographic analysis the product contains 87% monomethyl ether and 13% parent compound.

EXAMPLE IV 75 g (0.4 moles) of 2 methyl-2,4-pentanediol in THF reacts as with 38 g (0.8 moles) of 50% NaH and further with 14 g (0.1 moles) of $CuCl_2$ (advantageously the anhydrous $CuCL_2$ is added before NaH to the THF) and 18 ml (0.3 moles) of methyl iodide. Afte. the treatment described in Example I the yield before distillation is 80 g or almost quantitative and contains 83% of 2-O methyl ether and 11% methyl ether and 6% 2,4-di-O-methyl ether.

EXAMPLE V 9 g (0.1 moles) of 1,3 butanediol in DMF, 9,6 g (0,2 moles) of 50% sodium hydride, 14 g (0.1 moles) of $CuCl_2$ and 18 g (0.3 moles) of methyl iodide, when treated as in Example I, formed only monether, 54% of which was 1-O-methyl ether and 46% 3-O-methyl ether. 2,3-Butanediol chelate, which is produced from diol, sodium hydride and copper (II) chloride in the ratio 2:4:1, when treated in the same way, forms 94% monomethyl ether and 6% dimethyl ether.

EXAMPLE VI 11 g (0.1 moles) of pyrocathecol, 13.4 g (0.1 moles) of $CuCl_2$ and 9.6 g (0.2 moles) of 50% NaH formed in DMF under nitrogen athmosphere a chelate which reacted with 9 ml (0.15 moles) of methyliodide at room temperature in 30 minutes and gave 11 g or 90% yield of pyrocathecol-monomethyl-ether (=guaiacol).

EXAMPLE VII 2.8 g (0.01 moles) of methyl 4,6-O-benzylidene-α-D-glucopyranoside in DMF or in THF, 2,7 g (0.01 moles) of mercury (II) chloride and 1.0 g (0.02 moles) of 50% NaH gave a soluble chelate, which reacted with 2.0 g (0.02 moles) of acetic anhydride immediately at room temperature and gave a product consisting of 96% of 2-O-acetate, 1% 3-O-acetate and 3% of 2,3-di-O-acetate.

I claim:

1. A process for producing derivatives of hydroxyl compounds which have at least two hydroxyl groups or a hydroxyl group and at least one additional functional group, which is capable of forming polyvalent metal complexes, which comprises:
    a. forming a metal complex by reacting said hydroxyl or functional groups with a polyvalent metal compound, said reaction occurring in completely anhydrous conditions to form a metal complexed compound;
    b. subjecting the metal complexed compound to one or more further reactions selected from the group consisting of substitutions, addition, elimination, oxidation and reduction, which are selectively guided or limited by the presence of said metal complex, which acts either as a blocking group or as a guiding group, said further reactions also occurring in completely anhydrous conditions; and
    c. removing the metal complex to provide the desired reaction product.

2. A process according to claim 1, wherein said additional functional groups are essentially oxygen-containing groups.

3. A process according to claim 1 wherein said additional functional groups are groups which contain nitrogen or sulphur.

4. A process according to claim 1, wherein the reactions take place in a reaction-promoting organic anhydrous solvent solution.

5. A process according to claim 1, wherein the degree of ionization of the hydroxyl compound is controlled by a metal hydride, preferably sodium hydride, and the resultant alcoholate is reacted with a polyvalent metal compound in anhydrous condition to yield the corresponding metal derivative which is thereafter subjected to a further reaction in anhydrous conditions.

6. A process according to claim 1, wherein the parent hydroxyl compound and reaction products are recovered from the protecting metal derivative of said hydroxyl compound by the addition of water, acid or base.

7. A process according to claim 4, wherein the organic anhydrous solvent is recovered either before or after the addition of the water, acid or base to the reaction product.

8. A process according to claim 1 wherein the hydroxyl groups or other functional groups which have remained unreacted may be used for further reactions either before or after addition of water, acid or base, to the reaction mixture.

9. A process according to claim 1 wherein the reaction of the hydroxyl compound is guided to occur selectively or primarily at one or more functional groups affects either a non-masked hydroxyl or a metal oxygen bond in which case selective cleavage at one of the metal oxygen linkages follows. This leads to substitution of the revealed oxygen atom, while the blocking halide (or corresponding anion) is attached to the metal remaining at the other oxygen atom. Thus, e.g., —O—Cu—O— with methyl iodide forms —O—CH$_3$+I—Cu—O—. This selective blocking discerns even such small differences between the nature of the functional groups which would not guide the reactions by application of alkali alcoholates. Thus under anhydrous conditions, for example, the monosodium alcoholate of a diol primarily forms the mono-methyl ether in which the more acid alkoxyl group has reacted, while with chelates the copper actually protects the acid group giving the other mono-ether and thus no disubstitution at all. The disubstituted compound, in contradistinction, is always formed together with the monosubstituted compound when an alkali alcoholate is etherified.

SOLVENTS USED IN THE REACTION

The reaction with the polyvalent metal derivatives of hydroxyl compounds, according to this invention, takes place either in the anhydrous organic solvent or with the precipitated complex as such or the complex is transferred into another reaction-promoting anhydrous solvent. The following types of solvents are particularly suitable when completely anhydrous: ethers such as tetra- and dihydrofuran and their alkyl or alkoxyl derivatives, as well as tetra- and dihydropyrane with their derivatives. Furthermore, dioxanes and trioxanes may be used. Open chain ethers as 1,1 or 1,2-dimethoxyethane and 1,1,3,3-tetramethoxypropane. Dimethylformamide and other formamide-type solvents and dimethylsulphoxide and its derivatives are also suitable, as well as ketones such as acetone and nitrogen containing solvents as pyridine. In a few cases even hydrocarbons as benzene, into which the 1:2:1 chelate of a glucoside is soluble, and inert halogenated (chlorinated or fluorinated) hydrocarbons may be used.

METAL DERIVATIVES OF THE HYDROXYL COMPOUNDS

The alkali alcoholates are transformed into objects of reaction with salts of polyvalent metals. Cu, Ni, Co, Fe, Mn, Cr, V, Ti, Zn, Pd, Au, Hg, and U are advantageous. The recovery of the parent compounds of reaction products and unreacted compounds is achieved simply by adding water to the metal derivative mixture received after the reaction solvent has been distilled off.

REAGENTS

Organic halides and the esters of sulphuric acid are primarily used for etherification, and acid halogenides, acid anhydrides, and isocyanates for esterification. The reaction also takes place with other groups reacting with the O-atom, e.g., with epoxides. The chelates can also be oxidized and certain groups can be removed, e.g., by reduction.

SCOPE OF THE METHOD

The chelates can be used to achieve mono-substitution or generally a limited substitution which is lower than theoretical. Thus, e.g., the chelate 1:2:1 forms only a monosubstituted product but not a disubstituted one as does a mono- or di- alkali alcoholate for example. Accordingly, the chelates can be used for selective substitution to produce compounds which otherwise are formed only through multistage blocking and reconversion.

The chelates accentuate the steric and other differences of the hydroxyls in the substitution. Thus, by way of chelates, a cetain hydroxyl group can be selectively substituted with a removable masking group, e.g., as a benzyl group or as an acetate. After the addition of water, the unreacted hydroxyl group is free to use in further and now other exclusive reactions, as it was the case by the preceding one.

In a mixture of compounds with structure- or stereoisomeric hydroxyl compounds a reaction may be guided to affect either the chelate forming compound or the non-protected compound.

According to the method of the present invention, it is possible to limit the reaction of a hydroxyl compound exclusively to a certain degree of substitution or guide the reaction to occur selectively at a certain functional group or groups, by carrying out the reaction via a polyvalent metal derivative of the hydroxyl compound. Said reaction can be substitution, addition, elimination, oxidation or reduction, and can affect the metal derivative group as well as other parts of the molecule. The expression "substitution" means all those reactions where the hydrogen atom in the parent compound is substituted with other groups as in etherification, esterification etc. The expression in completely anhydrous conditions used in this application for the conditions of formation of the metal derivatives as well as the reactions in which these derivatives are used means that anhydrous reagents and solvents are used and that the reactions are protected against external humidity.

Figure 2:
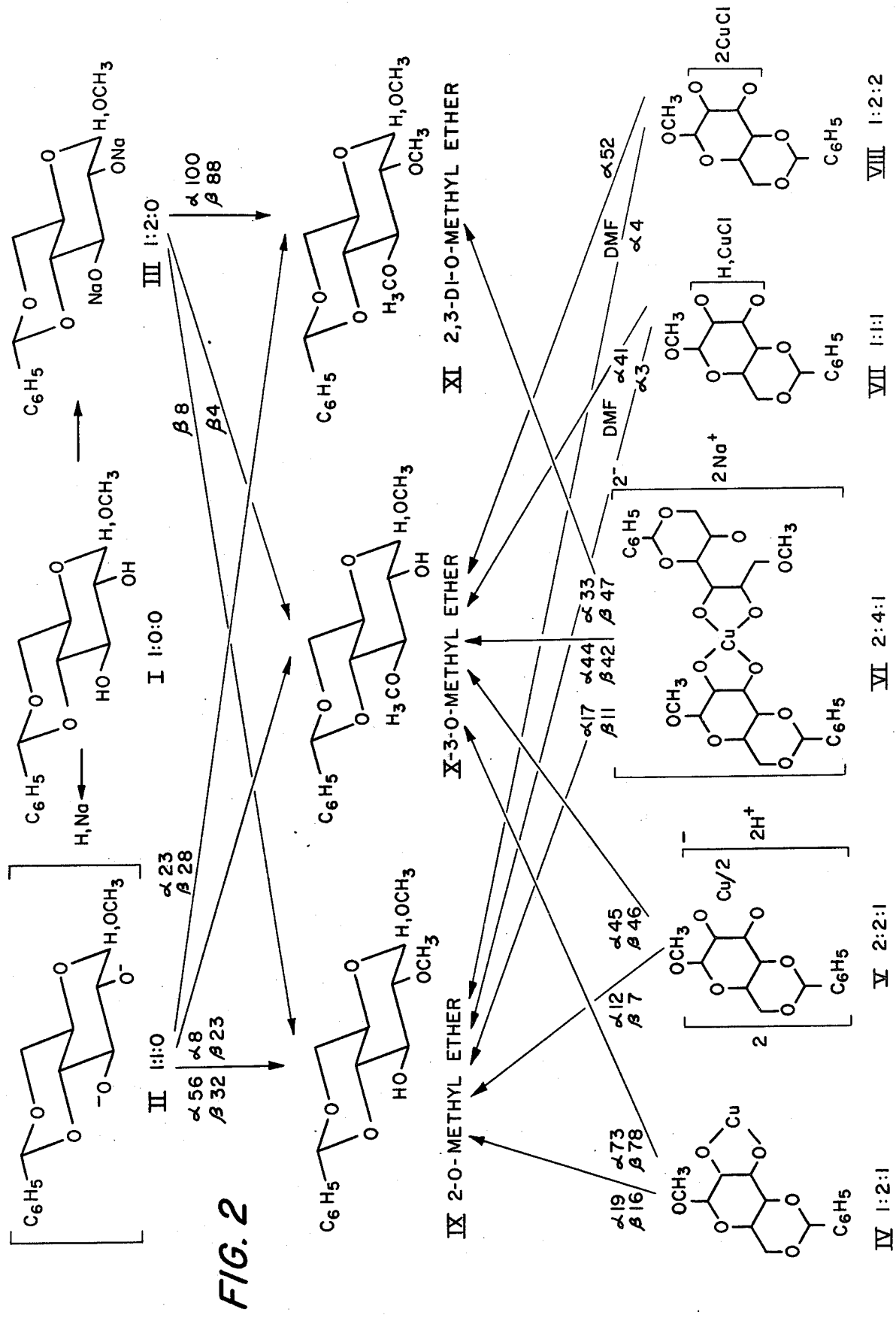

The above described reactions are illustrated in FIG. 2 which shows the methylation yields of anomeric 2-O-methyl-, (IX), 3-O-methyl-, (X), and 2,3-dimethyl-(Xl) ethers, which are formed from methyl 4,6-O-benzylidene-D-gluco pyranoside (I), when the corresponding mono- and di- sodium alcoholates (II and III); or copper (II) chelates (IV, V and VI) in tetrahydrofuran or copper (II) derivatives (VII and VIII) in dimethylformamide are reacted with methyl iodide. The yields are mole-%. The compounds are characterized by the mole ratio glucoside: NaH:CuCl$_2$ used in their preparation similarly as in the scheme of FIG. 1.

The following examples illustrate the invention:

EXAMPLE I 280 g. (1 mole) of methyl 4,6-O-benzylidene-α-D-glucopyranoside is dissolved in 2 litres of anhydrous tetrahydrofuran. 96 g. (2 moles) of sodium hydride as a 50% oil dispersion is added to the solution in small portions at room temperature, cooling the reaction mixture. After the addition of sodium hydride is finished the formation of alcoholate is completed in a few minutes at the boiling point of THF or about 2 hours at room temperature. To the resultant di-sodium alcoholate 134 g. (1 mole) of anhydrous copper (II) chloride is added, which immediately dissolves the white alcoholate precipitate to form a green clear chelate solution which thus is synthesized using the mole ratio of glucoside: sodium:copper of 1:2:1. 120 ml (2 moles) of methyl iodide (or dimethyl sulphate) is added to the solution. At room temperature 90% of the alpha anomer of the glucoside reacts in 5 days. Refluxed, sealed with a CaCl$_2$ tube, the reaction is completed in 15–20 hours. The prolonged treatment does not result in higher than mono-substitution.

subjecting the polyvalent metal derivate of the hydroxyl compound to the reaction.

10. A process according to claim 1, wherein said complex of a polyvalent metal is a chelate.

11. A method of using polyvalent metal complexes of hydroxyl compounds or compounds which have a hydroxyl group and at least one additional functional group as starting materials for subsequent selective reactions, which occur in anhydrous conditions, to yield derivatives of the hydroxyl compounds upon removal of the metal complexes.

12. A method according to claim 11 wherein the polyvalent metal complex is a chelate.

13. A method according to claim 11 wherein the additional functional groups are essentially oxygen containing groups.

14. A method according to claim 11 wherein the subsequent reactions to which the polyvalent metal complex of the hydroxyl compound is subjected are substitution, addition, elimination, oxidation and reduction.

15. A method according to claim 11 wherein the hydroxyl compound and reaction products are recovered from the protecting metal complexes of the hydroxyl compounds by the addition of water, acid or base to the reaction product.

16. A process according to claim 1, wherein said hydroxyl compounds are selected from the group consisting of polyhydric ether alcohols, hydroxy aldehydes, hydroxy ketones, diketones in the enol-form, polyketones, polyaldehydes, polyhydric phenols, phenol carboxylic acids and their derivatives, halogenated alcohols, hydroxy and ketoacids and their esters and derivatives of carboxylic acids.

17. A process according to claim 1, wherein said hydroxyl compounds are selected from the group consisting of 4,6-O-benzylidene-$\alpha$-D-glucopyranoside, triethylene glycol, 2 methyl-2,4-pentanediol, 1,3 butanediol and pyrocathecol, and the polyvalent metal compound is selected from the group consisting of anhydrous copper and cobalt chloride.

* * * * *

UNITED STATES PATENT AND TRADEMARK OFFICE
CERTIFICATE OF CORRECTION

PATENT NO. : 3,972,868
DATED : August 3, 1976
INVENTOR(S) : Eero Sakari Avela

It is certified that error appears in the above-identified patent and that said Letters Patent are hereby corrected as shown below:

First page, Abstract, delete "The present...certain purpose",

Column 1, lines 49 and 50, "example H.M., oligo" should read -- example mono-, oligo --.

Column 3, line 21, "1:2:, respectively" should read -- 1:2:2, respectively --

Column 3, line 50, "acheived" should read -- achieved --.

Column 4, line 40, "polyjydric" should read -- polyhydric --.

Column 6, line 5, "cetain" should read -- certain --.

Column 7, line 4, "protion concentrated" should read -- protion of concentrated --.

Columns 8 and 9, lines 68 and 1, "groups subjecting" should read -- groups by subjecting --.

Signed and Sealed this

Fourth Day of January 1977

[SEAL]

Attest:

RUTH C. MASON
Attesting Officer

C. MARSHALL DANN
Commissioner of Patents and Trademarks